United States Patent
Lee

(10) Patent No.: US 12,186,008 B2
(45) Date of Patent: Jan. 7, 2025

(54) SKIN CARE DEVICE USING RF NEEDLE

(71) Applicant: Eunsung Global Corp., Wonju-si (KR)

(72) Inventor: Ki Se Lee, Seoul (KR)

(73) Assignee: Eunsung Global Corp., Wonju-si (KR)

( * ) Notice: Subject to any disclaimer, the term of this patent is extended or adjusted under 35 U.S.C. 154(b) by 656 days.

(21) Appl. No.: 17/420,819

(22) PCT Filed: Dec. 31, 2019

(86) PCT No.: PCT/KR2019/018819
§ 371 (c)(1),
(2) Date: Jul. 6, 2021

(87) PCT Pub. No.: WO2020/149552
PCT Pub. Date: Jul. 23, 2020

(65) Prior Publication Data
US 2022/0087732 A1    Mar. 24, 2022

(30) Foreign Application Priority Data

Jan. 14, 2019 (KR) .......................... 10-2019-0004736

(51) Int. Cl.
*A61B 18/14* (2006.01)
*A61B 18/00* (2006.01)

(52) U.S. Cl.
CPC ...... *A61B 18/1477* (2013.01); *A61B 2018/00059* (2013.01); *A61B 2018/00452* (2013.01); *A61B 2218/007* (2013.01)

(58) Field of Classification Search
CPC ...... A61B 18/1477; A61B 2018/00059; A61B 2018/00452; A61B 2218/007
See application file for complete search history.

(56) References Cited

U.S. PATENT DOCUMENTS 8,025,673 B1 * 9/2011 Lyapko ............... A61N 1/0502
606/189

FOREIGN PATENT DOCUMENTS

| | | | |
|---|---|---|---|
| JP | 5410847 B2 | 2/2014 | |
| KR | 10-1300122 B1 | 9/2013 | |
| KR | 10-1587930 B1 | 1/2016 | |
| KR | 10-1669416 B1 | 10/2016 | |
| KR | 101713954 B1 * | 3/2017 | ............ A61N 1/403 |
| KR | 20180007365 A * | 1/2018 | ........ A61M 37/0015 |

(Continued)

OTHER PUBLICATIONS

Notification of Reason for Refusal for Korean Application No. 10-2019-0004736 mailed Jul. 16, 2020, with its English translation, 7 pages.

(Continued)

*Primary Examiner* — Linda C Dvorak
*Assistant Examiner* — Abigail Bock
(74) *Attorney, Agent, or Firm* — Christian S. Hans; Bret E. Field; Bozicevic, Field & Francis LLP

(57) ABSTRACT

A skin care device using an RF needle is disclosed. According to an embodiment, a skin contact part having a plurality of needles and a vacuum pressure formation unit for applying a suction force to the skin contact part are included, and thus a needle can be inserted into the skin by pulling the skin with vacuum pressure. Therefore, the skin is pulled with suction so that an equipment contact surface accurately comes into contact with the skin, and thus a needle can be correctly inserted into the inner layer of the skin.

2 Claims, 5 Drawing Sheets

(56) References Cited

FOREIGN PATENT DOCUMENTS

KR  10-2018-0078026 A  1/2019
KR  10-2018-0007365 A  4/2019

OTHER PUBLICATIONS

Decision to Grant a Patent for Korean Application No. 10-2019-0004736 mailed Nov. 25, 2020, with its English translation, 2 pages.

\* cited by examiner

[Fig. 1]
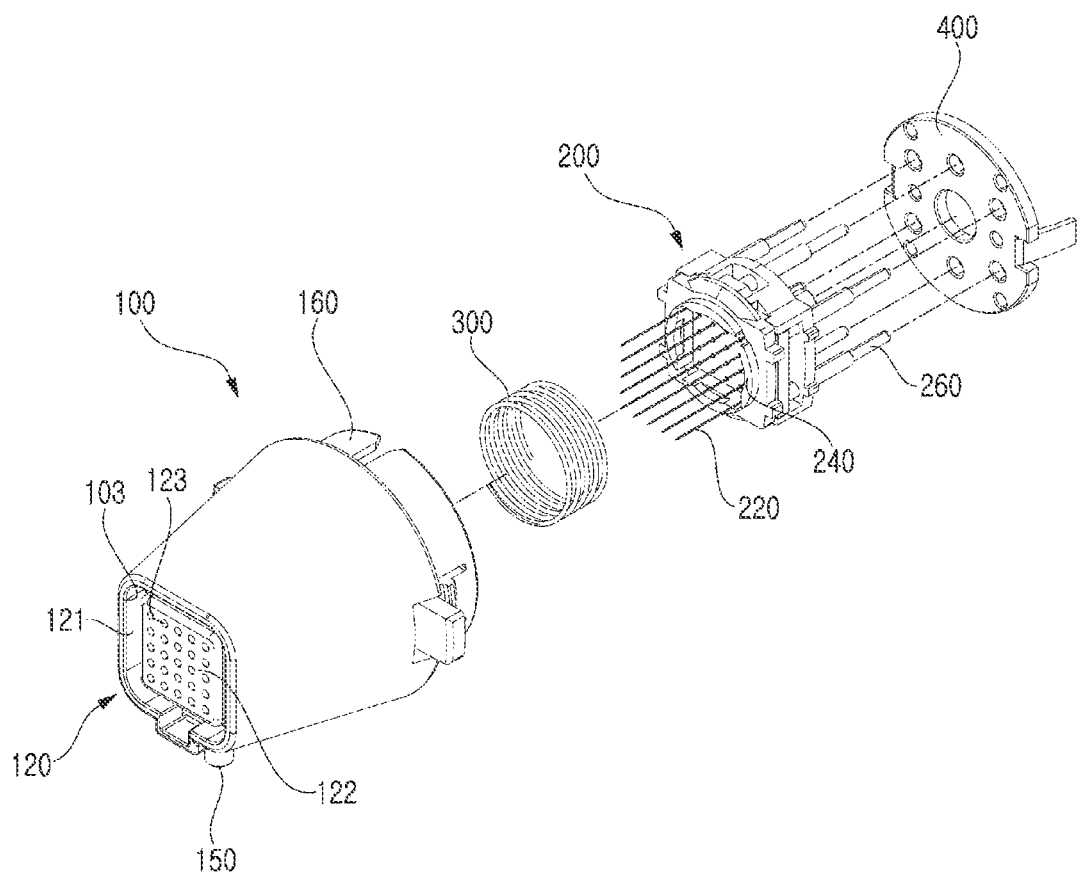

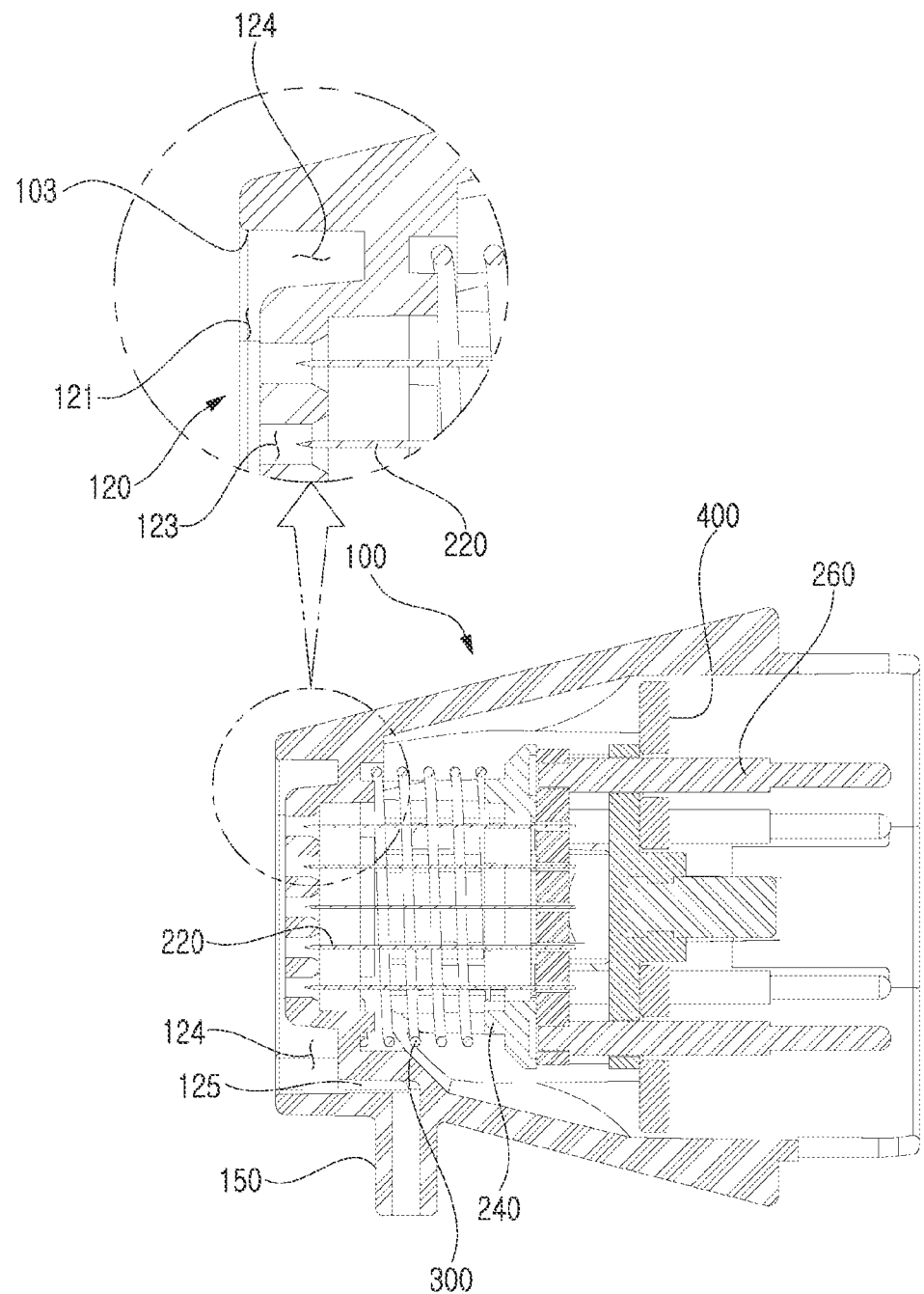

[Fig. 3]
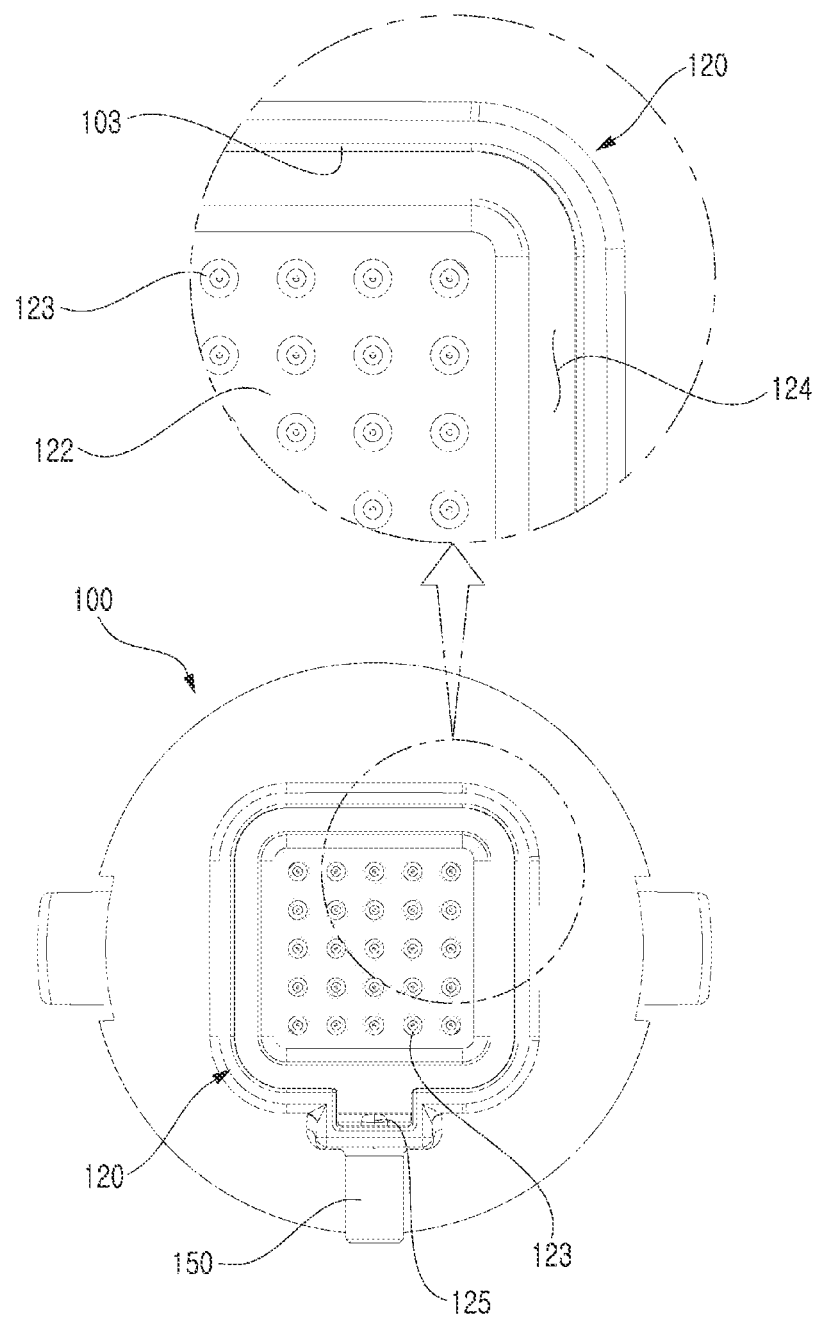

[Fig. 4]
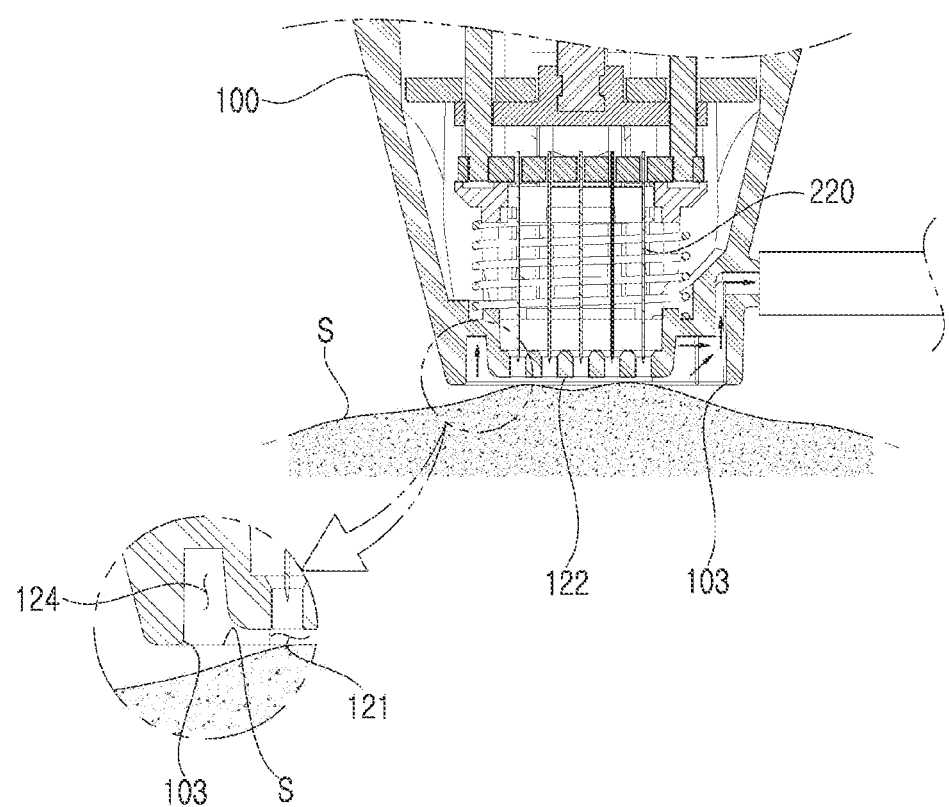

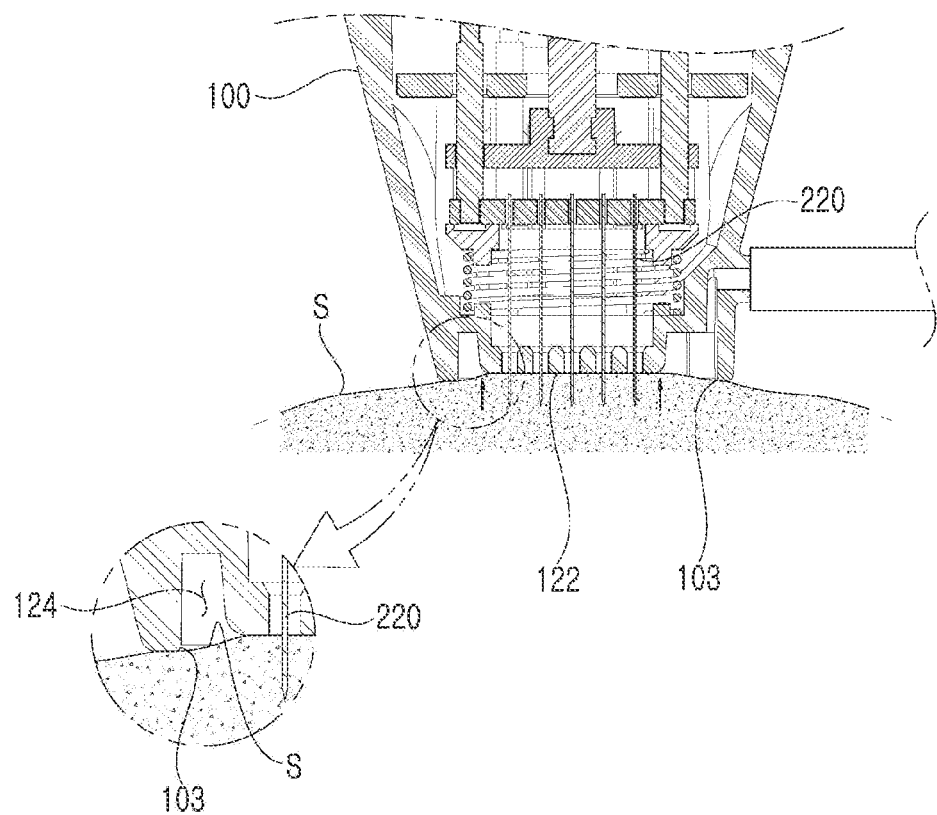
[Fig. 5]

SKIN CARE DEVICE USING RF NEEDLE

CROSS-REFERENCE TO RELATED APPLICATION

This Application is a Section 371 National Stage Application of International Application No. PCT/KR2019/018819, filed Dec. 31, 2019, the contents of which is hereby incorporated by reference in its entirety.

TECHNICAL FIELD

The present disclosure relates to a skin care device using a radio frequency (RF) needle. More particularly, the present disclosure relates to a skin care device using an RF needle, the skin care device being capable of applying various thermal effects to a skin tissue by applying an RF current and ultrasonically vibrating the needle so that electrical and physical energies are efficiently concentrated to a dermis layer.

BACKGROUND ART

Unless otherwise expressed in this specification, the contents described in this section are not related arts to the claims of the subject application. In addition, inclusion of an art in this section does not recognize the art as a related art.

Recently, technologies of improving skins by using various energy sources have been widely applied.

Currently, research has been actively conducted on skin treatment devices using a laser beam, a supersonic wave, and RF energy.

By using these technologies, energy is supplied into skin and heat is generated by a movement of molecules composing the skin tissue, and treatment effects such as improving skin elasticity or alleviating skin wrinkles can be realized by reorganizing a collagen layer by increasing a temperature inside the skin through the heat.

In conventional RF needle equipment, since a contact surface of equipment has not been precisely contacted with the user's skin due to a curvature of the skin while a treatment procedure was performed, there were problems in that a plurality of needles were not inserted into an inner layer of the skin to an appropriate depth and some needles were inserted to a shallow depth or not inserted.

DISCLOSURE

Technical Problem

Accordingly, the present disclosure has been made keeping in mind the above problems occurring in the related art, and an objective of the present disclosure is to provide a skin care device using a radio frequency (RF) needle, in which the skin care device allows the needle to be precisely inserted into an inner layer of a skin by pulling the skin with suction so that a contact surface of the device is in close contact with the skin precisely.

Technical Solution

According to an embodiment of the present disclosure, the objective of the present disclosure may be realized by the skin care device using the RF needle, in which the skin care device includes a skin contact part provided with a plurality of needles and includes a vacuum pressure formation unit for applying a suction force to the skin contact part, so that the skin is pulled by a vacuum pressure and the needles are capable of being inserted into the skin.

Advantageous Effects

According to an embodiment of the present disclosure, there is an effect in that the needles may be precisely inserted into an inner layer of a skin by pulling the skin with suction so that a contact surface of the device is in close contact with the skin precisely.

DESCRIPTION OF DRAWINGS

FIG. 1 is a side view illustrating a skin care device using a radio frequency (RF) needle according to an embodiment of the present disclosure.

FIG. 2 is a cross-sectional view illustrating a cartridge fixing portion of the skin care device using the RF needle according to an embodiment of the present disclosure.

FIG. 3 is a front view illustrating the cartridge fixing portion of the skin care device using the RF needle according to an embodiment of the present disclosure.

FIG. 4 is a view illustrating a state before an operation of the skin care device using the RF needle according to an embodiment of the present disclosure.

FIG. 5 is a view illustrating a state after an operation of the skin care device using the RF needle according to an embodiment of the present disclosure.

MODE FOR INVENTION

Hereinafter, exemplary embodiments of the present disclosure will be described in detail with reference to the accompanying drawings.

The embodiments to be described below are to describe the present disclosure in detail so that the present disclosure can be easily embodied by one of ordinary skill in the art to which this present disclosure belongs. However, this does not mean that the concept and scope of the present disclosure are not limited thereto.

In addition, the shapes and sizes of components in the drawings may be exaggerated for explicit and convenient description. Further, terms defined in consideration of configuration and function in the present disclosure may be varied according to the intention of a user, practice, or the like, so that the terms should be defined by the contents of this specification.

In the accompanying drawings, FIG. 1 is a side view illustrating a skin care device using a radio frequency (RF) needle according to an embodiment of the present disclosure. FIG. 2 is a cross-sectional view illustrating a cartridge fixing portion of the skin care device using the RF needle according to an embodiment of the present disclosure. FIG. 3 is a front view illustrating the cartridge fixing portion of the skin care device using the RF needle according to an embodiment of the present disclosure. FIG. 4 is a view illustrating a state before an operation of the skin care device using the RF needle according to an embodiment of the present disclosure. FIG. 5 is a view illustrating a state after an operation of the skin care device using the RF needle according to an embodiment of the present disclosure.

As illustrated in FIGS. 1 to 5, the skin care device using the RF needle according to an embodiment of the present disclosure includes: a head portion with which the cartridge fixing portion 100, a needle cartridge 200, an elastic body 300, and a cap 400 are assembled; a hand piece (not illustrated) to which the head portion is coupled and capable of being grasped by a user; and a vacuum pressure formation unit (not illustrated) configured to form a vacuum pressure on the head portion.

The cartridge fixing portion 100 is provided with a skin contact part 120 that is formed at a front side of the cartridge fixing portion 100 and has a plurality of needle holes 123, and a space is formed inside the cartridge fixing portion 100. A vacuum suction port 150 communicated with the skin contact part 120 and configured to generate a suction force is formed at a front outer circumferential surface of the cartridge fixing portion 100, and an opening portion is formed at a rear side of the cartridge fixing portion 100 and a coupling protrusion 160 is formed at the opening portion.

The skin contact part 120 includes: a recessed portion 121 concavely formed at a front end portion of the cartridge fixing portion 100; and a front surface plate 122 formed inside the recessed portion 121 and having the plurality of needle holes 123.

A stepped portion 103 is formed between the front end portion of the cartridge fixing portion 100 and the front surface plate 122 so as to have a height difference therebetween.

Thus, as illustrated in FIG. 2, a longitudinal distance of about 0.5 mm is formed between the front end portion of the cartridge fixing portion 100 and the front surface plate 122, so that a user's skin (S) may be close in contact with the front surface plate 122 by a suction force that allows the skin (S) to be inserted into the recessed portion 121.

The front surface plate 122 is placed by being concavely recessed from an outer circumferential edge surrounding thereof so that an outer circumferential groove 124 is formed, and a lower surface of the outer circumferential groove 124 and an inner side surface of the recessed portion 121 of the cartridge fixing portion 100 is connected to each other so as to be sealed.

Therefore, the outer circumferential groove 124 is formed in a ditch shape that is formed along the outer circumferential edge of the front surface plate 122, a hole 125 is formed on a portion of the outer circumferential groove 124, and the hole 125 is configured to communicate with the vacuum suction port 150.

The needle cartridge 200 is disposed in the space of the cartridge fixing portion 100, and is provided with a plurality of needles 220 that is configured to be inserted into the plurality of needle holes 123 of the skin contact part 120.

The elastic body 300 is coupled to an outer circumferential surface of the needle cartridge 200 and configured to provide an elastic force to the needle cartridge 200 by being inserted to the space of the cartridge fixing portion 100, and a coil spring is suitable for the elastic body 300.

In addition, the needle cartridge 200 has an annular protrusion 240 that protrudes from a front end portion of the needle cartridge 200, has the plurality of needles 220 inside the annular protrusion 240, has a plurality of injection tubes 260 that correspond to the plurality of needles 220, and a first end portion of the elastic body 300 is coupled to and fixed to the annular protrusion 240.

The cap 400 is inserted through the opening portion of the cartridge fixing portion 100 and has a plurality of through holes so as to allow the plurality of injection tubes 260 to be coupled thereto, and the cap 400 is coupled to the inside of the cartridge fixing portion 100 and is configured to seal same so as to allow the needle cartridge 200 and the elastic body 300 to be accommodated inside the cartridge fixing portion 100.

The vacuum pressure formation unit (not illustrated) includes a vacuum pump, and generates the suction force on the skin contact part 120.

Therefore, the vacuum pressure is formed at the cartridge fixing portion 100 and the skin is in close contact with the front surface of the skin contact part 120 by the vacuum pressure that pulls the skin, whereby the needles 220 may be inserted into the skin that is in close contact with the skin contact part 120.

Meanwhile, according to an embodiment of the present disclosure, the needles 220 have surfaces thereof coated with gold. Using gold to coat the needles, that is, using a needle that is not insulated by being gold-plated is advantageous over using a stainless steel needle that is insulated.

By emitting a radio frequency (RF) through the needles 220 that are gold-plated, the RF is inserted to the maximum penetration depth, and when an impedance of a dermis is lower than an impedance of an epidermis, the RF may flow through the dermis without a coagulation phenomenon of the epidermis.

Therefore, the needles 220 that are gold-plated provide better RF conductivity than that of stainless steel needles, so that a treatment effect may be improved.

In addition, an emission of the RF through the entire of the needles 220 that are gold-plated provides a coagulation effect that alleviates a microhemorrhage.

In other words, a gold-plated needle provides better RF conductivity than a stainless steel needle, so that a treatment effect may be improved.

Hereinafter, an operation of the present embodiment will be described.

As illustrated in FIG. 4, in a state of the vacuum pressure formation unit (not illustrated) being turned off, the needles 220 are in a state before being inserted into the skin.

Since a curved portion of the skin is spaced apart from the skin contact part 120, some of the needles are spaced apart from the skin or have a shallower insertion depth than that of other needles.

Therefore, the RF may not be uniformly reached to the dermis, which may cause a reduction of effectiveness in the treatment.

Next, as illustrated in FIG. 5, when the vacuum pressure formation unit is turned on, the vacuum suction force is formed at the recessed portion 121 of the skin contact part 120, so that the skin is pulled and inserted into the recessed portion 121 and is close in contact with the front surface plate 122. Therefore, since the skin is inserted into the skin contact part 120, there is no portion that is spaced apart from the front surface plate 122.

In this manner, the needle cartridge 200 moves forward and the needles 220 are drawn through the needle holes 123 with a state of the skin being in close contact with the front surface plate 122, so that the needles 220 may be inserted into the skin with a predetermined depth, thereby stably ensuring the effect of the treatment.

Although preferred embodiments of the present disclosure have been described for illustrative purposes, those skilled in the art will appreciate that various modifications, additions are possible, without departing from the scope and spirit of the present disclosure as disclosed in the accompanying claims, and it should be understood that the various modifications, additions are included within the scope of the accompanying claims.

DESCRIPTION OF REFERENCE NUMERALS

120: handle 140: head
200: skin contact part 220: needle

240: suction portion 242: hole
244: suction pathway

The invention claimed is:

1. A skin care device using a radio frequency (RF) needle, the skin care device comprising:
   a cartridge fixing portion having a front side provided with the skin contact part that is in contact with the skin and has a plurality of needle holes, the cartridge fixing portion having a space formed inside thereof, a front outer circumferential surface provided with a vacuum suction port that communicates with the skin contact part and is configured to generate a suction force, a rear side provided with an opening portion, and a coupling protrusion at the opening portion;
   a needle cartridge disposed in the space of the cartridge fixing portion and provided with a plurality of needles that is configured to be inserted into the needle holes of the skin contact part;
   an elastic body coupled to an outer circumferential surface of the needle cartridge and disposed in the space of the cartridge fixing portion, thereby providing an elastic force to the needle cartridge;
   a cap configured to seal the cartridge fixing portion by being coupled to the opening portion of the cartridge fixing portion; and
   a vacuum pressure formation unit configured to generate a suction force to the skin contact part,
   wherein the skin care device pulls a user's skin by using a vacuum pressure so that the skin is in close contact with a front surface of the skin contact part and allows the needles to be inserted into the skin that is closely contacted with the skin contact part,
   wherein the skin contact part comprises:
      a recessed portion formed at a front end portion of the cartridge fixing portion; and
      a front surface plate formed inside the recessed portion and having the plurality of needle holes,
   wherein the front surface plate is provided with an outer circumferential groove that is concave to an outer circumferential edge of the front surface plate, and a stepped portion is formed between the front end portion of the cartridge fixing portion and the front surface plate so as to have a height difference therebetween,
   wherein a hole is formed on a portion of the outer circumferential groove, the hole of the outer circumferential groove being configured to communicate with the vacuum suction port, and
   wherein the needle cartridge is provided with an annular protrusion that protrudes from a front end portion of the needle cartridge, the plurality of needles are formed inside the annular protrusion, a plurality of injection tubes are provided at a rear end portion of the needle cartridge so as to be corresponded to the plurality of needles, and a first end portion of the elastic body is coupled and fixed to the annular protrusion.

2. The skin care device of claim 1, wherein surfaces of the needles are coated with gold.

* * * * *